United States Patent [19]

Takatani et al.

[11] Patent Number: 5,203,329
[45] Date of Patent: Apr. 20, 1993

[54] NONINVASIVE REFLECTANCE OXIMETER SENSOR PROVIDING CONTROLLED MINIMUM OPTICAL DETECTION DEPTH

[75] Inventors: Setsuo Takatani, Houston; Jonathan P. Jaeb; Ronald L. Branstetter, both of San Antonio, all of Tex.; Hiroshi Sakai, Komaki, Japan

[73] Assignee: Colin Electronics Co., Ltd., Aichi, Japan

[21] Appl. No.: 805,003

[22] Filed: Dec. 11, 1991

Related U.S. Application Data

[63] Continuation-in-part of Ser. No. 417,321, Oct. 5, 1989.

[51] Int. Cl.$^5$ .................. G01N 33/49; A61B 5/00
[52] U.S. Cl. ..................................... 128/633; 356/41
[58] Field of Search ........................... 356/41; 128/633

[56] References Cited

U.S. PATENT DOCUMENTS

| | | | |
|---|---|---|---|
| 4,416,285 | 11/1983 | Shaw et al. | 356/41 |
| 4,867,557 | 9/1989 | Takatani et al. | 128/633 |
| 4,880,304 | 11/1989 | Jaeb et al. | 128/633 |

FOREIGN PATENT DOCUMENTS

| | | | |
|---|---|---|---|
| 0240742 | 1/1987 | European Pat. Off. | 356/41 |
| 3711272 | 10/1987 | Fed. Rep. of Germany | 128/633 |

OTHER PUBLICATIONS

Takatani et al. "A Noninvasive Tissue Reflectance Oximeter" *Annals of Biomedical Engineering*, vol. 8, No. 1 (1980) pp. 1–15.

Primary Examiner—Richard A. Rosenberger
Attorney, Agent, or Firm—Oliff & Berridge

[57] ABSTRACT

A noninvasive oximeter sensor for controlling and optimizing the minimum detection depth in the tissue of a patient is disclosed. In general, a minimum detection depth of 0.35 mm in the skin is considered optimum. The reflectance oximeter sensor component configuration of the present invention achieves the minimum detection depth. The present invention offers a more accurate indication of blood oxygen saturation in a patient's arterial blood than was available from previous reflectance oximeter sensors.

9 Claims, 7 Drawing Sheets

NONINVASIVE REFLECTANCE OXIMETER SENSOR PROVIDING CONTROLLED MINIMUM OPTICAL DETECTION DEPTH

This is a continuation-in-part application from application Ser. No. 417,321, filed Oct. 5, 1989.

FIELD OF THE INVENTION

The present invention relates generally to monitoring equipment which can be used to noninvasively estimate the degree of oxygen saturation of arterial blood. More specifically, the present invention provides an improved oximeter sensor comprising a geometric configuration which enables controlled minimum optical detection depth for a more accurate measurement of the blood oxygen saturation in the tissue.

BACKGROUND OF THE INVENTION

A pulse oximeter estimates noninvasively the degree of oxygen saturation of the hemoglobin in the arterial blood. Modern instruments use optical techniques in conjunction with a noninvasive sensor to achieve the estimate. The sensor of the oximeter radiates a section of well perfused tissue with at least two wavelengths of light. The light contacts hemoglobin contained in red blood cells. A certain amount of light is absorbed by the hemoglobin. The amount of light absorbed depends on the wavelength of light and the level of hemoglobin oxygenation. By knowing the wavelength of light being used and the relative amount of light being absorbed, it is possible to estimate the blood oxygen saturation.

Most of the currently available oximeters using optical methods to determine blood oxygen saturation are based on transmission oximetry. These devices operate by transmitting light of at least two wavelengths through an appendage such as a finger or an earlobe. By comparing the characteristics of the light transmitted into one side of the appendage with that detected on the opposite side, it is possible to compute oxygen saturations. A major disadvantage of transmission oximetry is that it can only be used on portions of the body which are thin enough to allow passage of light. Another disadvantage is, if the patient goes into shock, the extremities are the first to loose blood flow. If blood flow is lost, the oximeter cannot compute oxygen saturation.

There has been considerable interest in recent years in the development of an oximeter which is capable of using reflected light of at least two wavelengths to measure blood oxygen saturation. The sensor of such a device has the light source positioned on the same side of the tissue as the detector. In this configuration, the detector receives only that light which is scattered back (reflected) to the detector. The specific layout of the light source and detector is critical in optimizing the signal-to-noise ratio and thus improving the accuracy of the device.

A reflectance oximeter is especially useful for measuring blood oxygen saturation in portions of the patient's body which are not well suited to transmission measurements. However, a major disadvantage with previous reflectance oximeters has been that the oximeter sensors failed to offer a technique in which the detection depth in the tissue from which the light is reflected could be controlled and optimized. Without a technique in which the detection depth for the sensor can be optimized, a less accurate indication of blood oxygen saturation may result. Reflected signals are weaker than transmissive signals, and the previous reflective sensors have failed to provide a technique to optimize the detection depth in the tissue from which the reflected signals are received by the optical detector. Particularly, the ratio of the pulsatile component (AC) and average (DC) is important to improve the measurement accuracy. Specific sensor design based on the theoretical model is necessary to optimize such performance. The work by Takatani et al, "Experimental and Clinical Evaluation of Non-Invasive Reflectance Pulse Oximeter Sensor", Journal of Clinical Monitoring (accepted for publication), revealed that the larger the spacing between the light source and detector, the larger the AC/DC ratio. However, the larger the separation distance, the smaller the absolute signal level. The actual measurement in tissue revealed that separation distance of 3 to 4 mm will be optimum from an instrument point of view. In addition to optimizing the distance between the light source and the detector, optimization in controlling the detection depth is needed to minimize large background DC levels due to the skin layer adjacent to the sensor surface. The detection depth should be focused deeper than the adjacent skin layer which is approximately 0.3 to 0.5 mm.

Thus, there remains a strong need in the art for a noninvasive reflectance oximeter sensor in which the detection depth in the tissue may be controlled so that a more accurate indication of blood oxygen saturation is achieved.

SUMMARY OF THE INVENTION

Accordingly, the present invention has been developed to overcome the foregoing shortcomings of existing oximeter sensors.

It is therefore an object of the present invention to provide a reflectance oximeter sensor for which a minimum detection depth in the tissue may be controlled and optimized.

The minimum detection depth of light in the tissue is an important parameter when considering reflectance oximetry. In general, a minimum detection depth of 0.35 mm in the tissue is considered optimum. The reflectance oximeter sensor component configuration achieves the detection depth.

Thus, in accordance with the present invention, a method and apparatus is provided for controlling the minimum detection depth. An optical detector is optically isolated from the light source by an optical barrier. Light emitted by the source penetrates the tissue to some depth where it contacts hemoglobin and is subsequently scattered or reflected and then received by the detector. The particular distances between the barrier and the light source and between the barrier and the detector, the heights of the source and the detector, and the height and width of the optical barrier define a nominal minimum detection depth in the tissue that is viewed by the detector.

BRIEF DESCRIPTION OF THE DRAWINGS

The preferred embodiments are described with reference to the drawings in which.

DETAILED DESCRIPTION OF THE PREFERRED EMBODIMENTS

Figure 1:
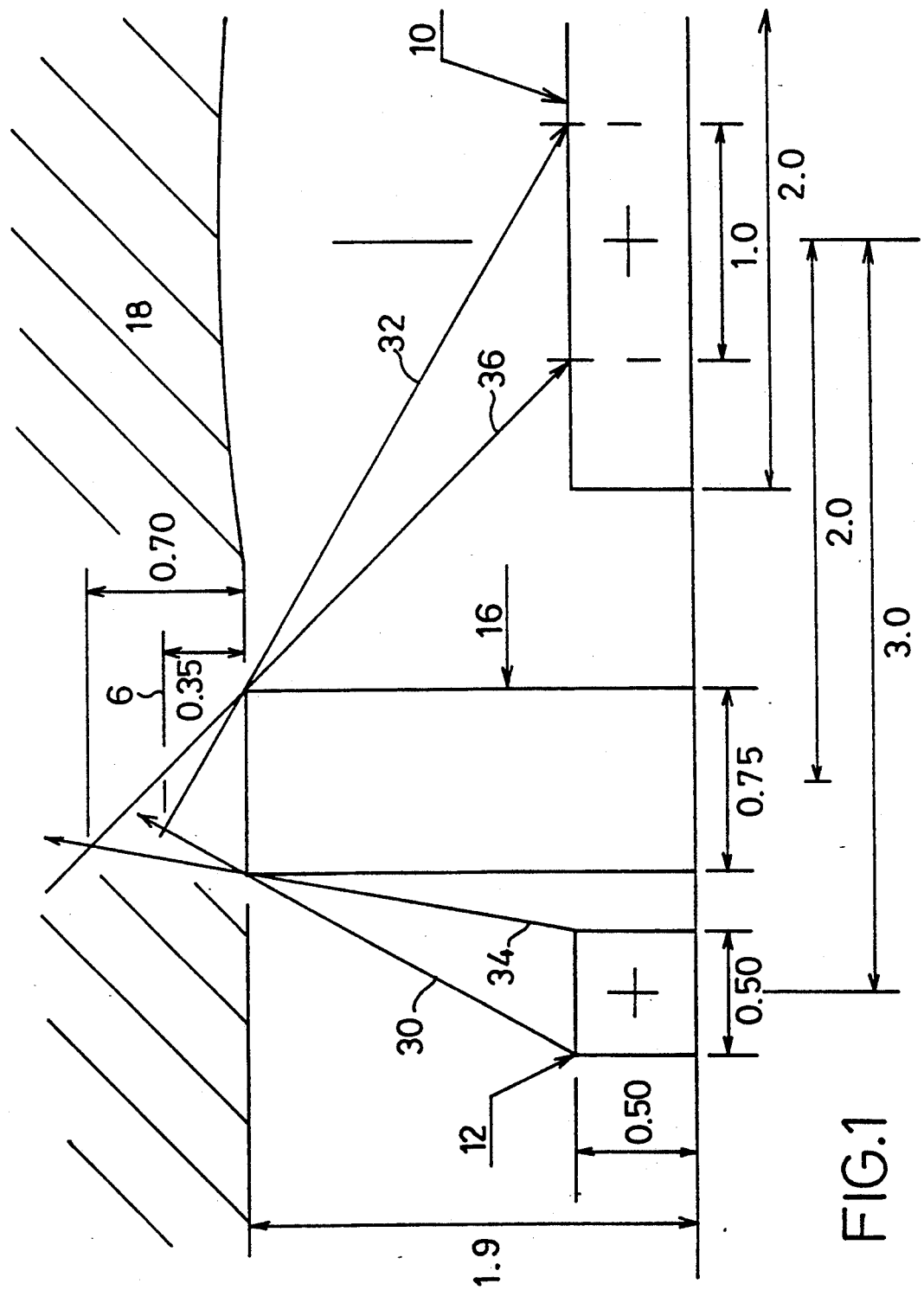
FIG. 1 is a geometric diagram of a minimum detection depth as created by a light source, optical barrier and optical detector in accordance with the present invention.

Referring to FIG. 1, shown is a minimum detection depth 6 which is established by the shown configuration for an oximeter sensor according to the preferred embodiment of the present invention. A light source 12, such as an LED, is represented as a square, measuring approximately 0.50 mm on each side. Optical barrier 16 is located adjacent the LED 12 and measures approximately 0.75 mm wide by 1.9 mm tall. Optical detector 10 is located adjacent to the optical barrier 16 and measures approximately 0.50 mm tall by 2.0 mm wide and has a light sensitive area approximately 1.0 mm wide centered at the center of the device. The center-to-center distance between the LED 12 and the detector 10 is approximately 3.0 mm. The center-to-center distance between the optical barrier 16 and the detector 10 is approximately 2.0 mm.

In the preferred embodiment, a ray of light 30 emitted from the left edge of LED 12 passes the left edge of optical barrier 16 and is at least partially reflected at a distance of 0.35 mm in the tissue or skin 18. After the reflection, the resulting ray 32 passes the right edge of the optical barrier 16 and is received at the right edge of detector 10. This 0.35 mm distance forms the minimum detection depth 6.

A second ray 34 emitted from the right edge of LED 12 passes the left edge of optical barrier 16, and is at least partially reflected at a depth of 0.70 mm in the skin 18. After such reflection, the resulting ray 36 passes the right edge of the optical barrier 16 and is received at the left edge of the detector 10. Thus, a deeper than 0.35 mm section in the skin 18 is viewed by the detector 10.

It is noted that FIG. 1 shows only one LED 12 as an example. However, there must be at least two LEDs of different wavelengths to effect a reflectance pulse oximeter as will be known by one of ordinary skill in the art. The second LED could be placed anywhere, so long as the above-described geometry is observed. For example, the optical barrier 16 could form a cylinder around the detector 10, with the LEDs of different wavelengths placed on opposite sides of the detector 10, outside of the optical barrier 16.

Figure 2:
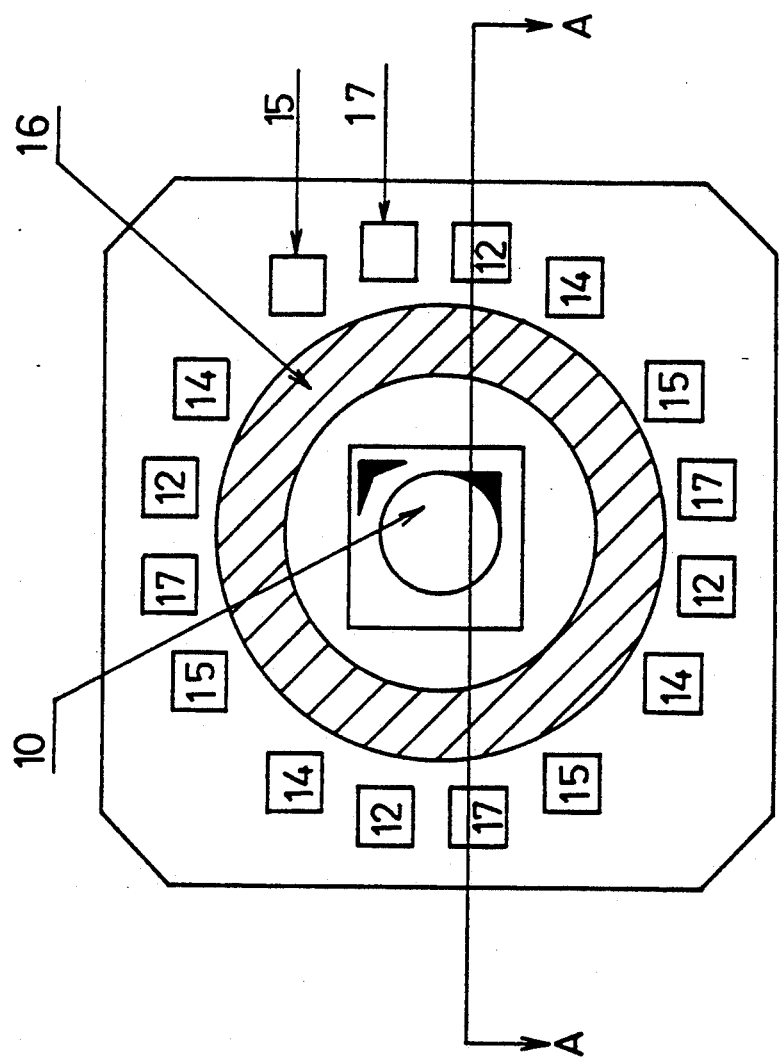
FIG. 2 is a plan view of one embodiment of the reflectance oximeter sensor in accordance with the present invention.

The method of the present invention is not limited to two LEDs. If it is desirable to use several LEDs, the LEDs could be placed in a circular ring around the outside of the cylindrical barrier 16 as shown in FIG. 2. A first set of LEDs 12 having a first particular wavelength are positioned equiangularly, i.e., at uniform increments about the circumference of the circular ring. A second set of LEDs 14 having a second wavelength are located alongside each of the first LEDs 12, at similar uniform increments in the same circular configuration. LEDs 15 and 17, having third and fourth wavelengths respectively, are similarly located until LEDs of all desired wavelengths are placed around the ring in an alternating fashion. Thus, the identical section of the skin 18 is radiated by each of the four wavelengths of light, and the signals reflected therefrom are received by the detector 10. FIG. 2 shows an embodiment of four LEDs of each of four wavelengths for a total of sixteen LEDs in the ring. Other embodiments may contain a different number of LEDs or desired wavelengths, so long as the above-described geometry is maintained to preserve the desired minimum detection depth.

Figure 3:
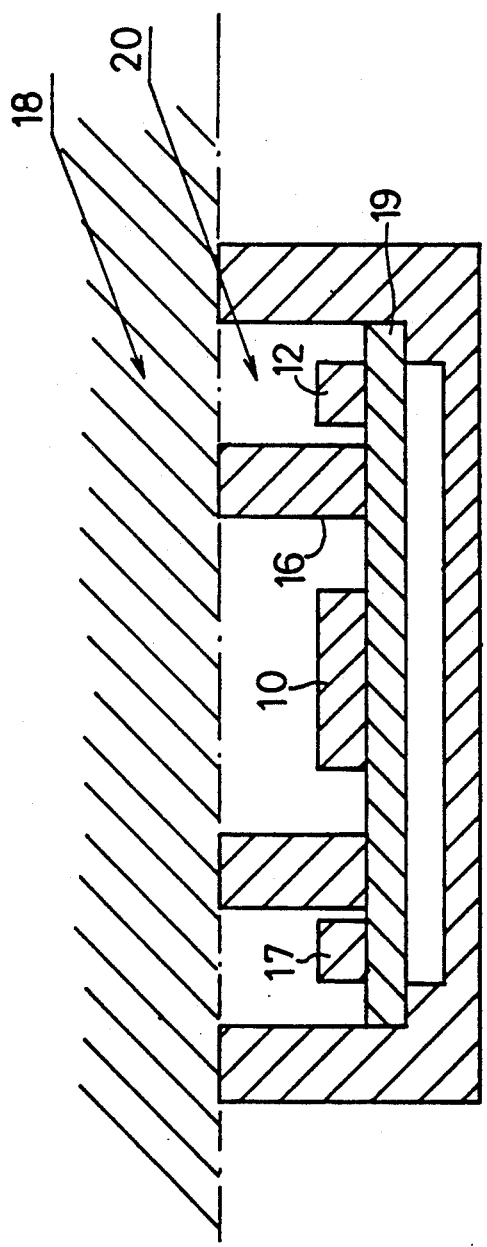
FIG. 3 is a cross-sectional view of the embodiment of the reflectance oximeter sensor taken along the line A—A of FIG. 2, in accordance with the present invention.

FIG. 3 shows the location of the skin 18 above the oximeter sensor and the location of an optically clear, mechanically hard material 20 placed for protecting the light sources 12, 14, 15, 17 and detector 10. In addition, the light sources 12–17, detector 10, and barrier 16 are secured to a planar surface of a support member 19.

In general, skin consists of epidermis, corium and subcutaneous tissue. The epidermis includes a horny layer at the external surface of the skin. The corium below the epidermis is composed of a dense network of fibrous connective tissue. The subcutaneous tissue below the corium includes fatty tissue. Arterial branches enter the skin from a horizontal plexus in the subcutaneous tissue, and form arteriolar plexus at the boundary between the subcutaneous tissue and the corium, or in the corium. From these arteries, capillary loops take origin and extend upward into the papillary layer of the corium. Venular plexus is distributed approximately in the same fashion as the artery system, and some of the venules combine each other into deep veins extending alongside arteries and others combine into cutaneous veins. A highly dense capillary plexus surrounds a hair follicle or sweat gland. The oximetry effected by the present oximeter sensor utilizes a pulsatile (AC) component contained in the signal (light) reflected by the arterial blood (hemoglobin). This AC component is much weaker than a constant (DC) component that usually arises from bloodless tissue elements. It is necessary to maximize the ratio of the AC component to the DC component for improving the accuracy of oxygen saturation measurement. To this end, it is desirable to obtain signals reflected from the boundary between the corium and the subcutaneous tissue or from the corium itself where arteriolar plexus is located. However, the intensity or magnitude of signals reflected from the skin is exponentially reduced as a function of depth in the skin. In other words, the signal reflected from the epidermis where no arteriolar plexus is located, has the greater magnitude than any other signals from the other layers of the skin. Accordingly, conventional oximeter sensors in which a minimum detection depth of light cannot be controlled or optimized, could not obtain signals having sufficient S/N (signal to noise) ratio or AD/DC ratio, and therefore might not determine blood oxygen saturation with high accuracy.

In contrast, in the present embodiment, the minimum detection depth 6 is selected at 0.35 mm in the skin 18 that is greater than the thickness of the epidermis, so as to increase the S/N ratio of the signals reflected from the skin 18. In other words, the signals reflected from the epidermis are not detected by the detector 10. According to "World Encyclopedia" (1972) published by Heibon-Sha Co. Ltd., Japan, the thickness of the epidermis of a human being generally ranges from 0.1 to 0.3 mm except for particularly thick skins such as of soles or palms. Therefore, the thickness of the epidermis of the skins from which the oxygen saturation is detected by the present oximeter sensor should be smaller than 0.35 mm. In addition, at the boundary between the epidermis and the corium, the arteriolar plexus is low in density and the arteries are small in diameter. In order to further improve the S/N ratio of the reflected signals, it is preferred that the minimum detection depth 6 be selected at not less than 0.5 mm for newborns and at 1.2 to 1.5 mm for adults.

In light of the present disclosure, it will be apparent to one of ordinary skill in the art that the minimum detection depth 6 can be controlled by changing the geometric configuration of optical detector 10, light source 12, and optical barrier 16. It is shown that the particular distance between the light source 12 and the detector 10, the particular distance between the light source 10 and the optical barrier 16, the heights of the source 12 and detector 10, and the height and width of the optical barrier 16, define a nominal minimum detection depth in the skin 18 that is viewed by the detector 10.

Figure 4:
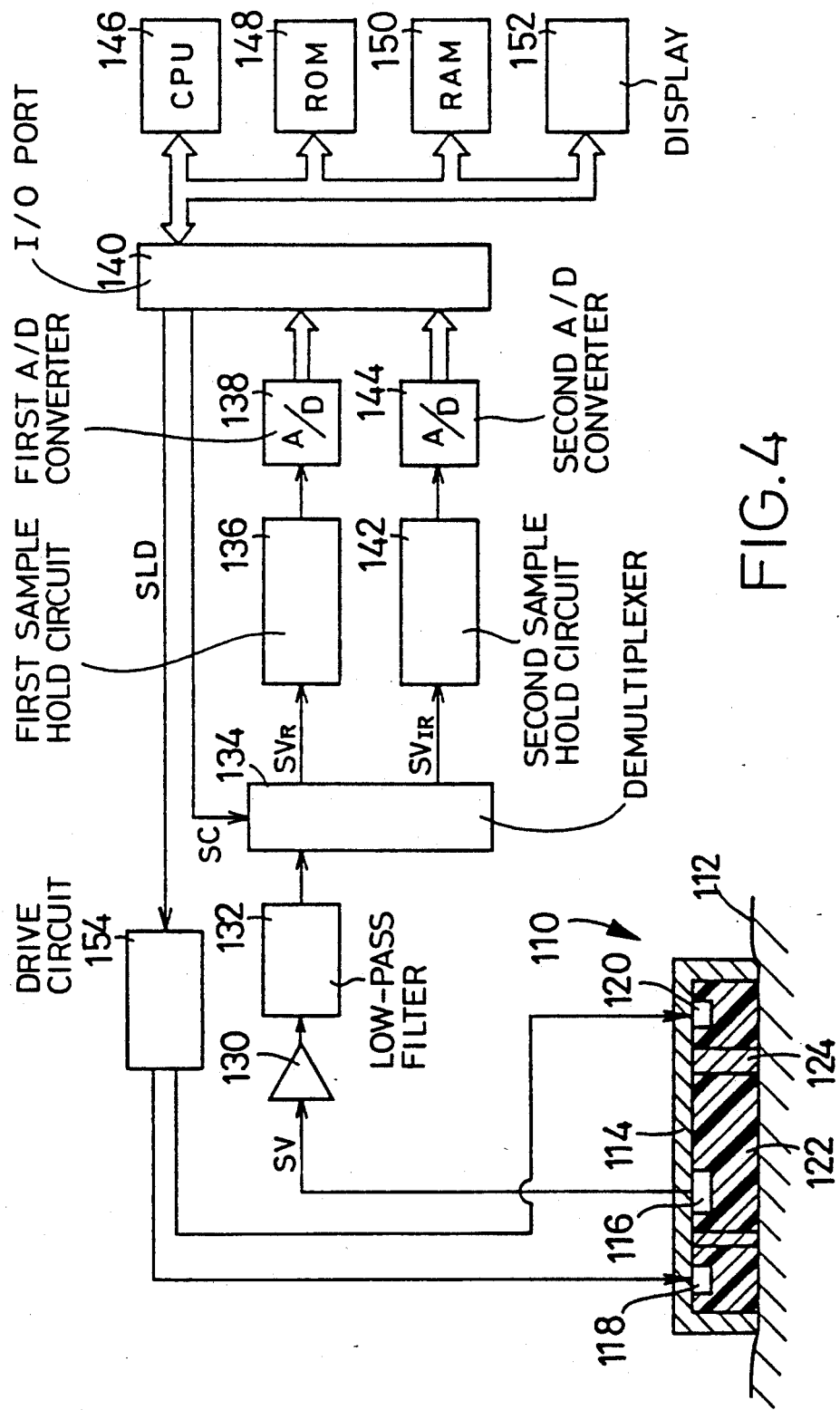
FIG. 4 is a block diagram of another embodiment of the present invention.
Figure 5:
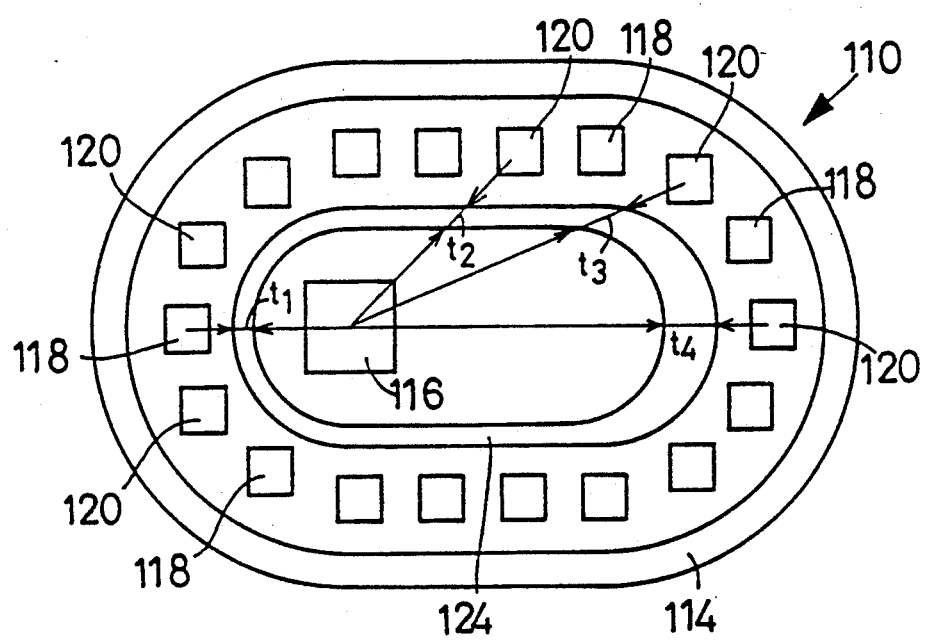
FIG. 5 is an enlarged view of a probe of the reflectance oximeter of FIG. 4, as viewed from the opening of a housing of the probe.

Referring next to FIG. 4, there is shown another embodiment of the invention. The present reflectance oximeter includes a detector probe 110 which is adapted to be set on the body surface 112 of a living subject, such as of a finger. As shown in FIGS. 4 and 5, the probe 110 includes a housing 114, a first and a second group of light emitting elements 118, 120, a light detecting element 116, and an optical barrier wall 124. The housing 114 has a container-like configuration with an elliptic bottom wall and an opening. Each of the two groups of light emitting elements 118, 120 includes, for example, nine light emitting diodes (LEDs) secured to the elliptic inner surface of the bottom wall of the housing 114. The light detector 116 is constituted by, for example, a photodiode or phototransistor, and is secured to the bottom wall of the housing 114 such that the nine LEDs of each of the two groups 118, 120 are located around the light detector 116 at equal distances from each other and such that the nine LEDs of the first group 118 are alternate with the nine LEDs of the second group 120. Consequently, the eighteen LEDs 118, 120 are disposed along an ellipse. The barrier wall 124 has an elliptic cylindrical shape, and is secured to the bottom wall of the housing 114, between the light emitters 118, 120 and the light detector 116, to prevent the light detector 116 from being illuminated by the lights emitted by the light emitters 118, 120 and subsequently reflected from the body surface 112. The probe 110 further includes a transparent resin member 22 filling the housing 114 to protect the light emitters 118, 120 and the light detector 116 by preventing those elements 118, 120, 116 from directly contacting the body surface 112.

The first light emitters 118 produce a red light of 660 nm, for example, while the second light emitters 120 produce a infrared light of 800 nm, for example. However, other pairs of different wavelengths may be employed so long as one wavelength exhibits significantly different absorption constants with respect to hemoglobin and oxygenated hemoglobin and the other wavelength exhibits substantially equal absorption constants with respect to the two sorts of hemoglobins. The two groups of light emitters 118, 120 alternately emit the red and infrared lights at a predetermined frequency, for a predetermined period of time for each emission. The lights emitted by the light emitters 118, 120 passes through the body surface 112, contacts blood in the blood bed, i.e., arteriolar plexus in the corium as a portion of the skin of the subject, and subsequently reflected therefrom. The reflected red and infrared lights are detected by the common light detector 116.

The light detector 116 generates an electric signal, SV, representing the magnitude of the detected red or infrared light, to a low-pass filter 132 via an amplifier 130. Signal SV contains a pulsatile (so-called "AC") component representing pulsation of arteries in synchronism with heartbeats of the subject. The low-pass filter 32 removes, from signal SV, noise having frequencies higher than the frequency of the pulsation, and the filtered signal SV is supplied to a demultiplexer 134. The demultiplexer 134 is switched between two positions thereof, in synchronism with the alternate emissions of the first and second light emitters 118, 120, according to switch signal, SC, which is described below. As a result, electric signals $SV_R$ corresponding to red lights are supplied to an input and output (I/O) port 140 via a first sample hold circuit 136 and a first analog to digital (A/D) converter 138, while electric signals $SV_{IR}$ corresponding to infrared lights are supplied to the I/O port 140 via a second sample hold circuit 142 and a second A/D converter 144. The sample hold circuits 136, 142 hold current signals $SV_R$, $SV_{IR}$ until the corresponding A/D converters 138, 144 complete the conversion of the preceding signals $SV_R$, $SV_{IR}$ into digital signals.

The I/O port 140 is connected via data bus to a central processing unit (CPU) 146, a read only memory (ROM) 148, a random access memory (RAM) 150, and a display 152. The CPU 146 effect blood oxygen saturation measurement by utilizing the temporary-storage function of the RAM 150 according to control programs pre-stored in the ROM 148. More specifically, the CPU 146 produces emit signal, SLD, to a drive circuit 154 via the I/O port 140 so that the first and second light emitters 118, 120 alternately emit red and infrared lights at a predetermined frequency, for a predetermined period of time for each emission. Concurrently, the CPU 146 produces switch signal SC in synchronism with the emissions of the red and infrared lights so as to switch the multiplexer 134 between its two positions. Consequently, red light signals $SV_R$ are supplied to the first sample hold circuit 136, while infrared light signals $SV_{IR}$ are supplied to the second sample hold circuit 142. In addition, the CPU 146 operates for determining a blood oxygen saturation of the subject based on signals $SV_R$, $SV_{IR}$ according to the programs pre-stored in the ROM 148, and indicating the determined value on the display 152. The determination method employed in the present oximeter is described in detail in Japanese Patent Application laid open under Publication No. 3(1991)-15440. Briefly, an actual blood oxygen saturation is determined based on an actual value of the ratio represented by the following formula (I), according to a predetermined relationship between ratio (I) and blood oxygen saturation:

$$\frac{(V_{dR} - V_{sR})/(V_{dR} + V_{sR})}{(V_{dIR} - V_{sIR})/(V_{dIR} + V_{sIR})} \quad (I)$$

In the ratio (I), $V_{dR}$ and $V_{sR}$ indicate an upper and a lower peak value of the waveform represented by red light signals $SV_R$, respectively, and $V_{dIR}$ and $V_{sIR}$ indicate an upper and a lower peak value of the waveform represented by infrared light signals $SV_{IR}$, respectively; therefore, $(V_{dr} - V_{sR})$ and $(V_{dIR} - V_{sIR})$ indicate the respective amplitudes of the two waveforms, and $(V_{dR} + V_{sR})$ and $(V_{dIR} + V_{sIR})$ indicate two times the magnitudes of the respective static (so-called "DC") components of the two waveforms.

The housing 114 includes an elliptic side wall corresponding to the elliptic bottom wall thereof. The light detector 116 is disposed, inside the elliptic cylindrical barrier 124, at a position nearer to one of the two centers of the ellipse than the other center. Thus, distances between the light detector 116 and the nine LEDs of each of the two light emitter groups 118, 120, are different from each other. Therefore, the light detector 116 and the nine LEDs of each group 118, 120 cooperate with each other to define different optimum detection depths, $d_{opt}$, as measured from the body surface 112, from which red or infrared light having a sufficient intensity is reflected. That is, the present probe 110 provides, for each of the red and infrared lights, a suitable detection depth having a sufficient width equal to the range of the different optimum detection depths with respect to the nine LEDs of each group 118, 120.

Figure 6:
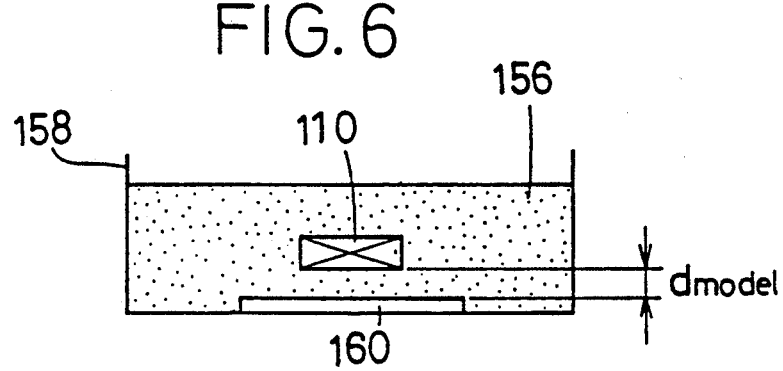
FIG. 6 is a view of a model of living tissue which model is used for examining the probe regarding the capability of detecting reflected light.
Figure 7:
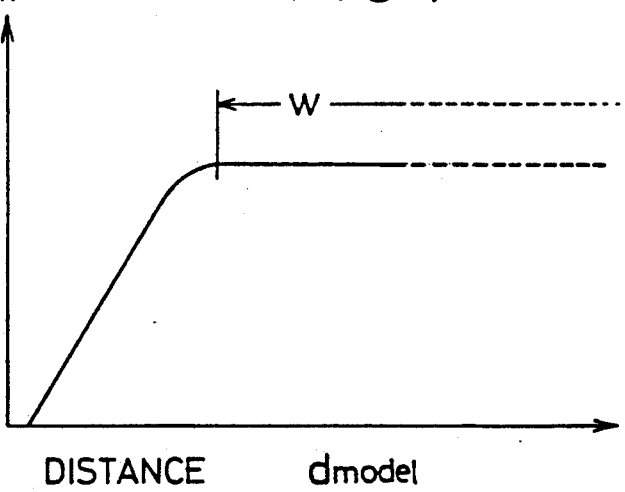
FIG. 7 is a graph showing the test result obtained by using the model of FIG. 6; .
Figure 8:
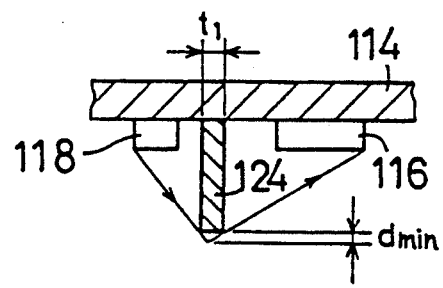
FIG. 8 is a view for explaining a minimum detection depth, $d_{min}$, with respect to a portion of an optical barrier member of the probe of FIG. 5 which portion has a thickness, $t_1$.
Figure 9:
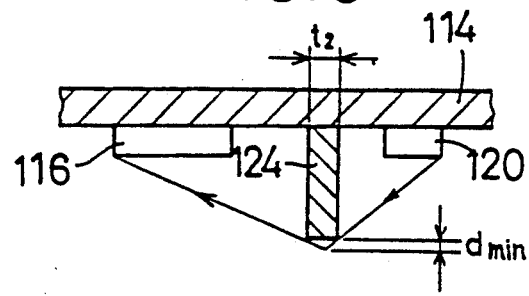
FIG. 9 is a view for explaining a minimum detection depth $d_{min}$ with respect to a portion of the optical barrier member which portion has a thickness, $t_2$.
Figure 10:
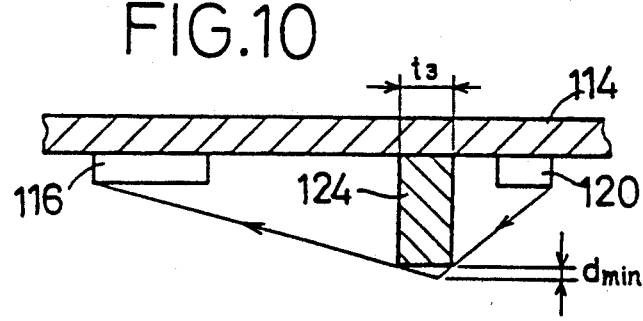
FIG. 10 is a view for explaining a minimum detection depth $d_{min}$ with respect to a portion of the optical barrier member which portion has a thickness, $t_3$.
Figure 11:
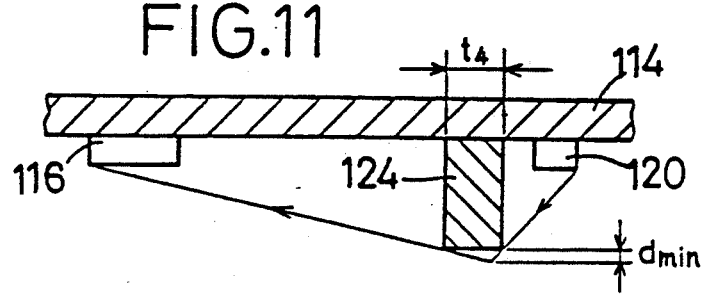
FIG. 11 is a view for explaining a minimum detection depth $d_{min}$ with respect to a portion of the optical barrier member which portion has a thickness, $t_4$.

FIG. 6 shows a model of tissue of a living body, in which a reflecting mirror 160 is immersed in a suspension 156, such as milk, received in a container 158. The model is used for examining the probe 110 regarding the capability of detecting reflected lights. In the examination, the light emitters 118, 120 are driven to emit lights toward the reflecting mirror 160 in the suspension 156 while at the same time a distance, $d_{model}$, between the probe 110 and the mirror 160 which distance corresponds to the detection depth in the living tissue as measured from the body surface 112) is varied at a predetermined rate. FIG. 7 shows a curve representing the variation in intensity of the reflected lights detected by the detector 116. The curve has a plateau, W, having a sufficiently great width. Plateau W indicates a suitable detection depth from which an optimum intensity of reflected light is detected by the detector 116. From this test result, it is estimated that, when the present probe 110 is applied to living tissue, the probe 110 provides a suitable detection depth $d_{suit}$ having a sufficient width or range.

FIG. 5 shows that, as the distances between the light detector 116 and the nine LEDs of each group 118, 120 are increased, thicknesses, t, of corresponding portions of the elliptic barrier wall 124 as measured in directions of straight lines connecting between the detector 116 and the respective LEDs are increased as shown at $t_1$ to $t_4$ in the figure. Thus, each of the eight LEDs of each group 118, 120, a corresponding portion of the optical barrier wall 124, and the light detector 116 cooperate with each other to define, under the body surface 112, a common or equal minimum detection depth, $d_{min}$, of, for example, 0.35 mm, as shown in FIGS. 8 through 11.

In the present embodiment, the height of the barrier wall 124 is constant.

In the embodiment shown in FIGS. 4-11, the light emitters of each of the two groups 118, 120 are located around the light detector 116 such that the distances between the detector 116 and the respective light emitters are different from each other. For this reason, the present oximeter sensor provides a large range or width of suitable detection depth $d_{suit}$. Therefore, in spite of differences in depth of the blood bed or arteriolar plexus among individual subjects or different sites or tissues of a subject, a sufficiently great intensity of reflected light signal $SV_R$, $SV_{IR}$ is obtained. Particularly, it is the AC/DC ratio, not the absolute intensity, for each wavelength which is optimized for accurate measurement of blood oxygen saturation. Consequently, accurate blood oxygen saturation measurement is effected based on the thus obtained good signals. In the case where a subject goes into shock because of, for example, application of a surgical knife or administration of a medicine and accordingly the subject is under lowered peripheral blood circulation, lights can be reflected only from deeper portions of the blood bed. Even in such cases, the present oximeter sensor can detect reflected light signal $SV_R$, $SV_{IR}$ with sufficient intensity or magnitude, assuring that blood oxygen saturation is measured with high accuracy and reliability.

Since the common minimum detection depth $d_{min}$ is selected at 0.35 mm that is greater than the thickness of epidermis of almost all skin, the light detector 116 is prevented from detecting the lights reflected by the epidermis in which no blood vessel is located. This arrangement contributes to increasing the ratio of the AC component to the DC component, i.e., $(V_{dR} - V_{sR})/(V_{dR} + V_{sR})$ or $(V_{dIR} - V_{sIR})/(V_{dIR} + V_{sIR})$, thereby improving the accuracy of blood oxygen saturation measurement.

Other modifications and variations to the invention will be apparent to those skilled in the art from the foregoing disclosure and teachings. It is therefore to be understood that, within the scope of the appended claims, the invention may be practiced otherwise than as specifically described. Thus, while only certain embodiments of the invention have been specifically described herein, it will be apparent that numerous modifications may be made thereto without departing from the spirit and scope of the invention.

What is claimed is:

1. A reflectance oximeter sensor for achieving a controlled minimum detection depth in the skin of a living subject, the reflectance oximeter sensor comprising:
    a plurality of light source means for producing lights of different wavelengths at different times, respectively, toward the skin of a subject;
    a single optical detector means for detecting the lights reflected from said subject,
    optical barrier means disposed between said plurality of light source means and said optical detector means, for preventing the detector means from being illuminated by the lights reflected by an external surface of said skin; and
    each of said plurality of light source means, a corresponding portion of said optical barrier means, and said optical detector means cooperating with each other to define, in said skin, a common minimum detection depth greater than a thickness of epidermis as a portion of said skin, wherein said common minimum detection depth is not less than 0.50 mm, said optical detector means detecting the lights reflected from a deeper portion of said skin under said minimum detection depth.

2. The oximeter sensor as set forth in claim 1, wherein each of said plurality of light source means comprises a plurality of light source elements located at uniform increments along a circle at the center of which said optical detector means is located, and said optical barrier means comprises a cylindrical wall member at the center of which said optical detector means is located.

3. The oximeter sensor as set forth in claim 2, wherein the light source elements of said each light source means are located at uniform increments along said circle, alternatively with the light source elements of each of the other light source means.

4. The oximeter sensor as set forth in claim 1, further comprising a support member having a planar surface, said detector means, said plurality of light source means, and said optical barrier means being secured to said planar surface of said support member.

5. The oximeter sensor as set forth in claim 4, further comprising protective means for protecting said optical detector means and said plurality of light source means, each secured to said planar surface of said support member, by preventing contact thereof with said skin, said protective means being formed of an optically clear, mechanically hard material.

6. The oximeter sensor as set forth in claim 1, wherein said common minimum detection depth falls within a range of 1.20 to 1.50 mm.

7. A reflectance oximeter sensor for measuring a blood oxygen saturation of a living subject by utilizing lights of different wavelengths reflected from tissue of the subject, comprising:
  a plurality of light source means for emitting lights of different wavelengths at different times, respectively, toward tissue of a subject;
  a single optical detector means for detecting the lights of different wavelengths reflected from said subject, and generating an electric signal representing the detected magnitude of each of the reflected lights;
  each of said plurality of light source means comprising a plurality of light source elements which are disposed around said optical detector means such that distances between the detector means and each of said light source elements are different from each other;
  optical barrier means disposed between said plurality of light source means and said optical detector means, for preventing the detector means from being illuminated by the lights reflected by an external surface of said tissue, said optical barrier means having a generally annular configuration; and
  each of said light source elements of each of said plurality of light source means, a corresponding portion of said optical barrier means, and said optical detector means cooperating with each other to define a common minimum detection depth as measured from said external surface of said tissue, said optical detector means detecting the lights reflected from a deeper portion of said tissue under said common minimum detection depth.

8. The oximeter sensor as set forth in claim 7, wherein said optical barrier means comprises an elliptic cylindrical wall, said elliptic cylindrical wall having, at different portions thereof, different thicknesses as measured in directions connecting between said optical detector and said light source elements of each of said plurality of light source means, so as to provide said common minimum detection depth.

9. The oximeter sensor as set forth in claim 7, wherein said common minimum detection depth is not less than 0.35 mm.

* * * * *